US00PP29706P3

(12) United States Plant Patent
Lange

(10) Patent No.: US PP29,706 P3
(45) Date of Patent: Sep. 25, 2018

(54) ***CITRUS* TREE NAMED 'LANGE ROSY RED VALENCIA'**

(50) Latin Name: *Citrus sinensis*
Varietal Denomination: Lange Rosy Red Valencia

(71) Applicant: Nancy B. Lange, San Francisco, CA (US)

(72) Inventor: Nancy B. Lange, San Francisco, CA (US)

( * ) Notice: Subject to any disclaimer, the term of this patent is extended or adjusted under 35 U.S.C. 154(b) by 0 days.

(21) Appl. No.: 15/530,079

(22) Filed: Dec. 1, 2016

(65) Prior Publication Data

US 2018/0160585 P1 Jun. 7, 2018

(51) Int. Cl.
*A01H 5/08* (2018.01)
*A01H 6/78* (2018.01)

(52) U.S. Cl.
USPC ..... Plt./202
CPC ..... *A01H 6/78* (2018.05); *A01H 5/08* (2013.01); *A01H 5/0806* (2013.01)

(58) Field of Classification Search
USPC ..... Plt./201, 202
CPC ..... A01H 5/0806
See application file for complete search history.

*Primary Examiner* — Kent L Bell
(74) *Attorney, Agent, or Firm* — Knobbe, Martens, Olson & Bear LLP

(57) ABSTRACT

A new and distinct *citrus* tree variety 'Lange Rosy Red Valencia' is characterized by a strong reddish blush of the rind of its fruit. The blush is present through the harvest and post-harvest and is concomitant with the color of the flesh. The flesh of the fruit has a persistent pinkish red color and produces a distinctive pinkish-red colored juice. The internal and external color persists and increases as the fruit matures. The new variety 'Lange Rosy Red Valencia' also presents dimorphism of the leaf pattern, structure and presence of leaf variegation that distinguish it from other 'Valencia' orange varieties. The new variety 'Lange Rosy Red Valencia' is similar to the sweet orange variety 'Cara Cara' in that both have internal pinkish red flesh. The harvest season for the 'Cara Cara' begins roughly in December and ends generally by the end of April, while the optimal harvest season for 'Lange Rosy Red Valencia' begins in May and finishes at the end of August. Besides the seasonality, the new variety 'Lange Rosy Red Valencia' differs from 'Cara Cara' and 'Olinda Valencia' in that the 'Lange Rosy Red Valencia' has a rind with a distinctive pinkish red blush.

5 Drawing Sheets

Latin name of the genus and species claimed: *Citrus sinensis.*

Variety denomination: 'Lange Rosy Red Valencia'.

BACKGROUND AND SUMMARY

This invention relates to the discovery and asexual propagation of a new and distinct variety of *citrus* tree, *Citrus sinensis* cv. 'Lange Rosy Red Valencia'. The new variety was discovered as a spontaneous mutation at the distal portion of a single sport limb on an 'Olinda Valencia' orange tree by Nancy B. Lange. The 'Olinda Valencia' orange tree on which the sport limb was discovered is estimated to be over 60 years old and is located in a cultivated grove of 'Olinda Valencia' orange trees in the San Joaquin Valley, Calif.

The new variety 'Lange Rosy Red Valencia' was discovered in April, 2009. It was asexually reproduced by budding the new variety onto 'Carrizo' rootstock (unpatented). The new *citrus* variety 'Lange Rosy Red Valencia' was first asexually propagated by Nancy B. Lange in the San Joaquin Valley, Calif. in the spring of 2012. The new variety 'Lange Rosy Red Valencia' has maintained its characteristics through succeeding asexual reproduction.

The new variety 'Lange Rosy Red Valencia' is a sweet orange *citrus* tree and is most notable for the internal pinkish-red flesh of the fruit and pinkish-red juice. The rind of the fruit of the new variety 'Lange Rosy Red Valencia' has a distinct red blush with tinges of orange and light green. The fruit maturation and harvest window for the new variety 'Lange Rosy Red Valencia' is May through August in the Central Valley of California. The fruit is found throughout the trees on the fruiting laterals. The trees grow vigorously and the fruits are round and uniform in symmetry.

The new variety 'Lange Rosy Red Valencia' has new leaves that are pale, green and variegated. However, as they mature the leaves become greener and the variegation is visible but less distinct. The majority of the leaves are falcate, and rarely obovate-oblanceolate, or elliptic. The leaf tips are typically rounded, and rarely mucronate or truncate. Proximal to the fruit and flowers the leaves are smaller than the leaves on vegetative branches.

Figure 4:
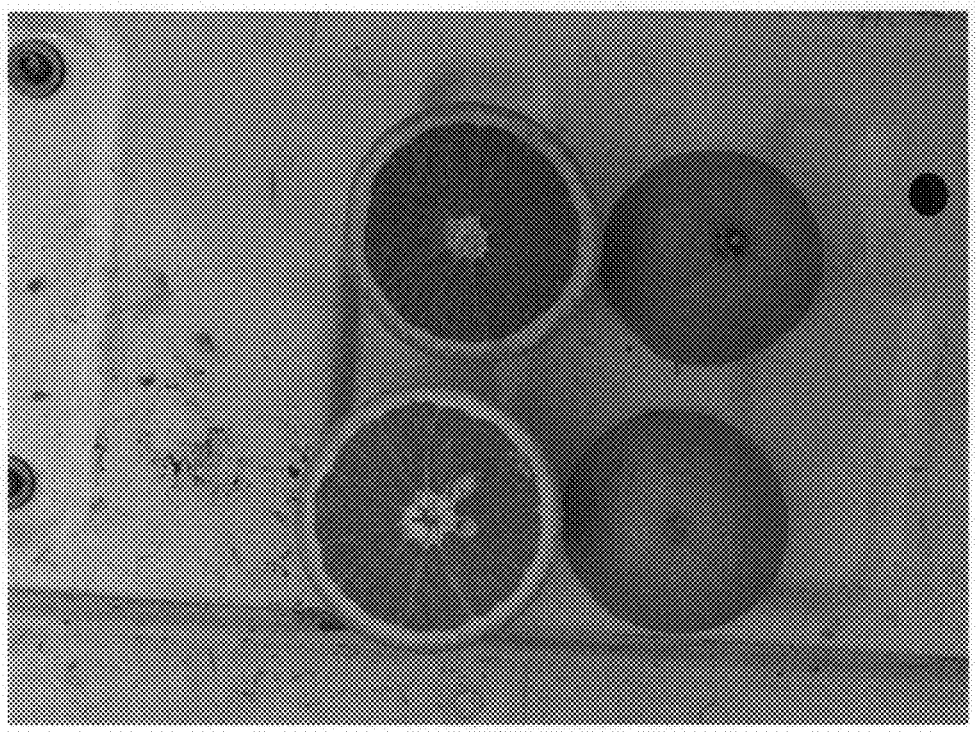
Figure 5:
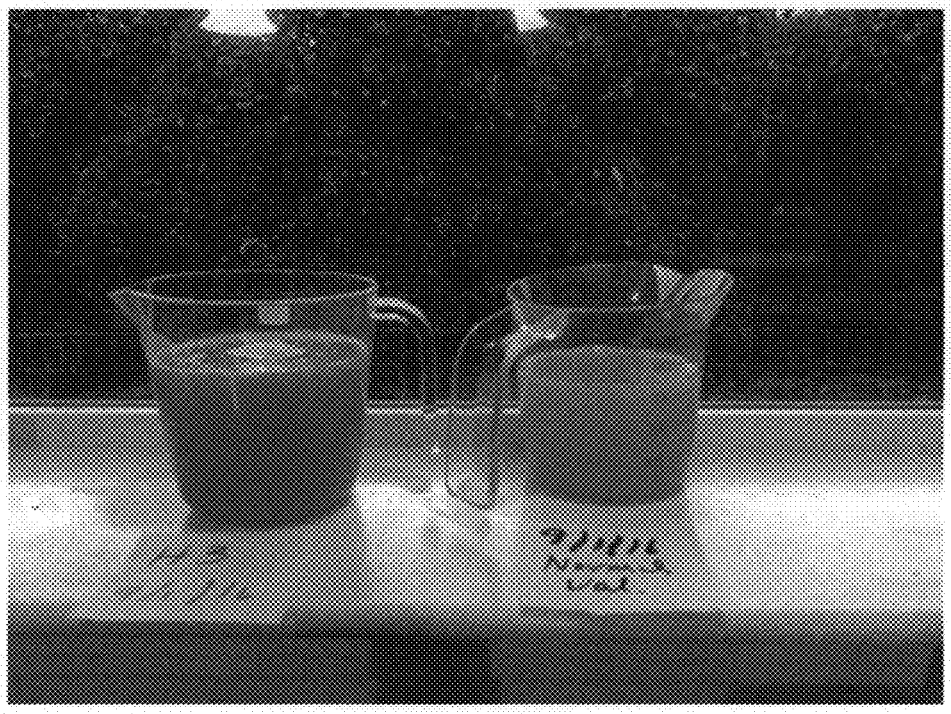

In contrast to the 'Olinda Valencia' variety, which has fruit with an orange-colored rind and orange-colored flesh, and produces orange colored juice, the fruit of the new variety 'Lange Rosy Red Valencia' has pinkish-red flesh (FIG. 4), a rind with pink red blush and produces distinctive pinkish-red juice (FIG. 5). The rind coloration changes as the fruit matures. In April the rind is orange with a pink blush. By August the rind coloration increases and is a darker reddish blush with little orange coloration at all. On some fruit, there is some re-greening of the rind beginning roughly in the middle of June and persists. The new variety 'Lange Rosy Red Valencia' also presents dimorphism of the leaf pattern, structure and presence of leaf variegation (FIG. 3) that distinguish it from other 'Valencia' orange varieties. The new variety 'Lange Rosy Red Valencia' and the navel orange variety 'Cara Cara' are similar in that both are derived as a spontaneous mutation on a sport limb and the fruit of both varieties has pinkish-red internal flesh. However, the new variety 'Lange Rosy Red Valencia' is distinguished from 'Cara Cara' in that the fruit of 'Cara Cara' has an orange rind like other navel varieties in the marketplace. The fruit of 'Lange Rosy Red Valencia' has a rind with a distinctive reddish tint (FIG. 1) and a reddish pink juice (FIG. 5) that makes it easily distinguished from other 'Valencia' varieties and 'Cara Cara' varieties. In addition the 'Cara Cara' is a winter orange, with the fruit harvested from December to April, while the new variety 'Lange Rosy Red Valencia' is a summer variety harvested from May through August.

The new variety 'Lange Rosy Red Valencia' has been shown to maintain its distinguishing characteristics through successive asexual propagations by, for example, budding.

BRIEF DESCRIPTION OF THE PHOTOGRAPH

The accompanying color photographic illustrations were taken shortly after the fruit was picked and the colors are as nearly true as is reasonably possible in a color representation of this type.

Figure 1:
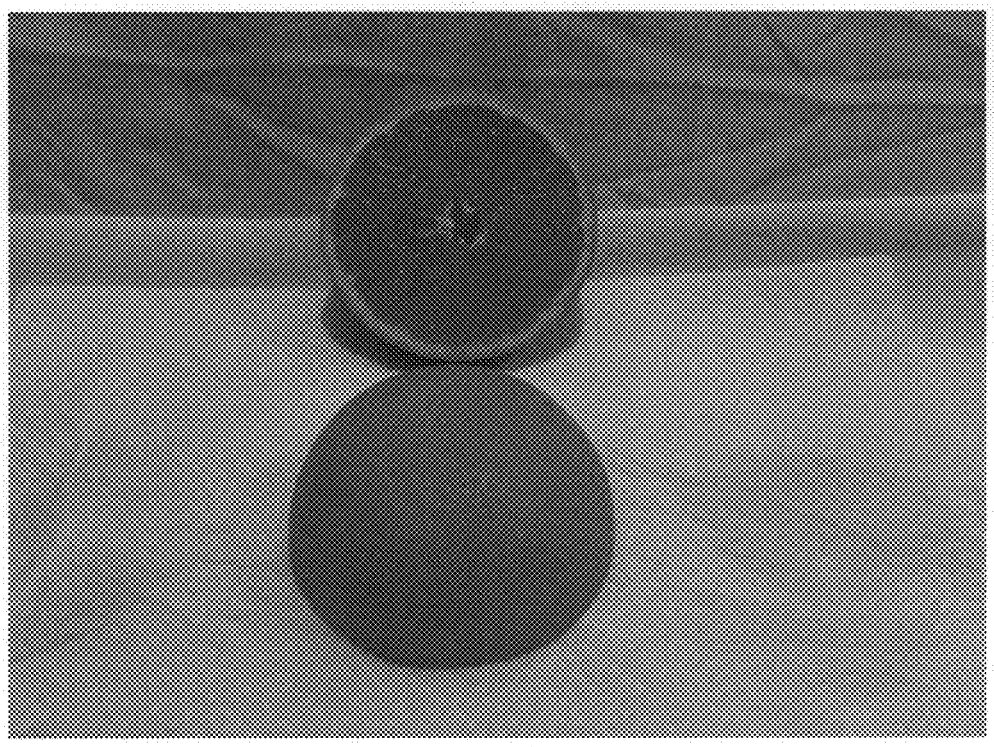

FIG. 1 shows the fruit of the new variety 'Lange Rosy Red Valencia' cut in half illustrating the internal pinkish red flesh and reddish blush of the rind.

Figure 2:
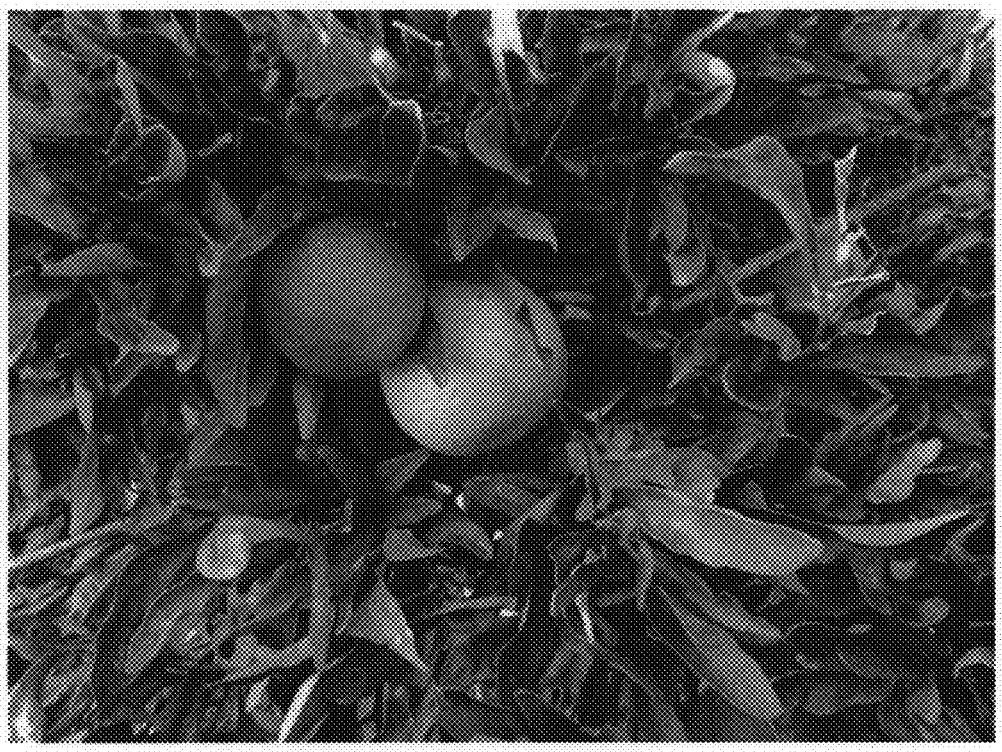

FIG. 2 taken in October 2016 shows typical specimens of the foliage and ripe and unripe fruit of the new *citrus* variety 'Lange Rosy Red Valencia'.

Figure 3:
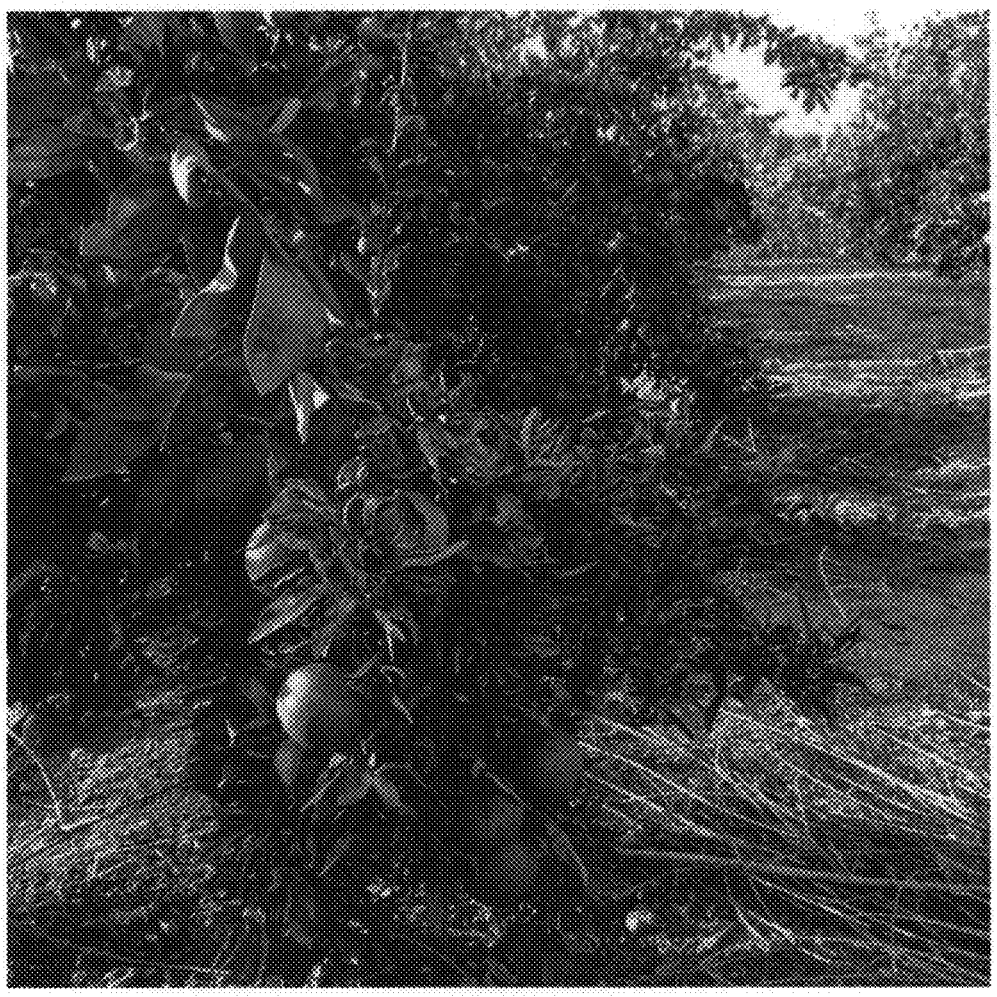

FIG. 3 taken in October 2016 shows typical specimens of the foliage and unripe fruit of the new *citrus* variety 'Lange Rosy Red Valencia'.

FIG. 4 taken on April 2016, shows a cross-section of the fruit of the new variety 'Lange Rosy Red Valencia' in comparison with the fruit of 'Olinda Valencia' which is the variety of the mother tree.

FIG. 5 shows the distinctive pinkish-red juice from 'Lange Rosy Red -Valencia' fruit in comparison with juice from 'Olinda Valencia' fruit.

DETAILED DESCRIPTION OF THE PREFERRED EMBODIMENT

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986. Common color names are also occasionally used.

The descriptive matter which follows pertains to 4 year old 'Lange Rosy Red Valencia' trees, grown in San Joaquin Valley, Calif., and is believed to apply to trees of the variety grown under similar conditions of soil and climate elsewhere. The characteristics of the 'Lange Rosy Red Valencia' trees and fruit were observed during the first fruiting season of 326 trees propagated from budwood of the mother limb. Daughter trees, propagated in April 2012, and granddaughter trees, propagated in January 2013, were planted in March 2014 at two different sites in the San Joaquin Valley, Calif. The fruit testing and tree observations were made on the daughter trees at test site number one.

TREE:

General: (Measurements taken are the average of measurements taken on 8 daughter trees).

- *Size*.—Medium, when compared to other commercial sweet orange cultivars of similar age.
- *Vigor*.—Medium to vigorous.
- *Growth*.—Semi-upright with branches spreading both vertically and horizontally, not drooping.
- *Productivity*.—Productive. Fruit counts averaged 71 fruits per tree second harvest season.
- *Form*.—Rounded top with some dominate upright branch shoots.
- *Bearer*.—Regular.
- *Fertility*.—Self-fertile.
- *Canopy density*.—Dense. The branches have clusters of numerous small sized leaves.
- *Hardiness*.—The present tree was grown and evaluated in USDA hardiness zone 9b 25 to 30° F.
- *Height*.—Average of 2.4 meters (measurement taken on trees planted March 2014).
- *Width*.—Average of 2.1 meters (measurement taken on trees planted March 2014).

Trunk:

- *Diameter*.—Approximately 16 cm measured 4 cm above the bud graft. The largest diameter measured was 18.5 cm and the smallest was 14 cm.
- *Texture*.—Medium smooth with vertical lenticels.
- *Trunk color*.—About Medium Greyed-Brown 199C and about Medium Greyed-Orange 164C.
- *Lenticels*.—Approximately 7 to 8 per $cm^2$.

Branches:

- *Size*.—Medium.
- *Diameter*.—Approximately 11 cm measured at first bifurcation at the top of the trunk. The largest measured diameter was 16 cm and the smallest was 8 cm.
- *Average length*.—Approximately 1.1 meters.
- *Surface texture*.—Mostly smooth.
- *Color of mature branches*.—Main scaffold branch is about Medium Greyed-Green Group 197C. The secondary branches about Medium Greyed-Green 197C and Light Greyed-Green 197D plus Medium Greyed-Brown 199B.
- *Color immature branches*.—Tertiary branches are about Medium Yellow-Green 146A with the most immature branches are about Medium Yellow-Green 146 B.
- *Lenticels*.—Present.
- *Thorns*.—Present and sparse. They are present on some branches and completely absent on others. Thorns when present are of varying lengths from approximately 0.5 cm to 4.4 cm. The average thorn length when present is approximately 2.3 cm.
- *Color of thorns*.—About Medium Yellow-Green 148A and Medium Yellow-Green 148B.

Lenticels:

- *Number*.—Numerous. The long dimension of the lenticel runs along the trunk and along the long dimension of the branches.

*Density*.—The scaffold branches contain approximately 10 per $cm^2$, and the secondary branches contain approximately 12 per $cm^2$. Tertiary branches have few lenticels.

*Color*.—Varies with the maturity of the branch. The mature branches are about Medium Greyed-Green 197D and the younger branches are about Medium Greyed-Brown 199D.

*Size*.—Large and elongated.

*Length*.—Approximately 2 mm to 10 mm.

*Width*.—0.3 mm.

FOLIAGE

Leaves: There is a dimorphic leaf pattern based on consistent differences of the size and shape of the leaves.

Type 1 leaves: These leaves are small, compact and falcate and are found on fruiting branches. Nodes of the fruiting branches display a leaf or one or two small branches from which multiple leaves are born (alternate arrangement). The leaves appear bunched up or clustered around the fruits. Type 1 leaves are variegated, particularly when juvenile and expanding. As they mature the variegation is less prominent as the leaves develop a deeper green pigmentation.

*Size*.—Small.

*Average length*.—Approximately 4.7 cm.

*Average width*.—Approximately 1.5 cm.

*Color of upper surface of variegation portion of the leaf*.—About Medium Yellow-Green 145 B and Light Yellow-Green 145C.

*Color of upper surface of non-variegation*.—Background portion of the leaf is about Medium Yellow-Green 144A.

*Color of the lower surface*.—About Medium Yellow-Green 145A.

*Color of petioles*.—About Medium Yellow-Green 145B and about Medium Yellow-Green 146C.

*Form*.—Mostly falcate with uneven borders resulting in a wrinkling of the leaf.

*Tip*.—Acuminate.

*Base*.—V-shaped.

*Margin*.—Repand.

*Venation*.—Pinnate.

*Vein color*.—About Medium Yellow-Green 145B.

*Surface texture*.—Glabrous, both upper and lower surfaces.

*Leaf blade* (*ratio of length to width*).—About 3:1.

*Profile*.—Up folded.

*Leaf blade tip*.—In the plane of the leaf.

*Angle of tip*.—Mostly acute.

*Undulation of margin*.—Pronounced.

Type 1 petiole:

*Average length*.—Approximately 0.85 cm.

*Average diameter*.—Approximately 1.0 mm.

*Color*.—About Medium Yellow-Green 1458 and about Medium Yellow-Green 146C

*Thickness*.—Slender.

*Type* 2 leaves: These leaves are larger, falcate, sometimes elliptic or oblanceolate. The leaves are alternate on the stem and appear more like "traditional" *citrus* leaves. These leaves may appear on a single uniform branch, or be part of a branch that also has the clustered leaves. These portions of leaves may occur along the fruiting branch for a certain portion or at the end of a fruiting branch. They have minimal variegation or none at all.

*Size*.—Large.

*Average length*.—Approximately 7.4 cm.

*Average width*.—Approximately 3.2 cm.

*Color of upper surface of mature leaves*.—About Medium Yellow-Green 146A and about Medium Yellow-Green 147B .

*Color of the lower surface of mature leaves*.—About Medium Yellow-Green 145A.

*Color of veins of mature leaves upper surface*.—About Medium Yellow-Green 146B.

*Color of veins of mature leaves lower surface*.—About Light Yellow-Green 145C.

*Color of upper surface of young leaves*.—About Medium Yellow-Green 144C.

*Color of lower surface of young leaves*.—About Medium Yellow-Green 145B.

*Color of vein upper surface young leaves*.—About Medium Yellow-Green 145B.

*Color of vein lower surface of young leaves*.—About Medium Yellow-Green 152C.

*Form*.—Mostly falcate, some obovate, oblanceolate, rarely elliptic.

*Tip*.—Acuminate some mucronate.

*Base*.—V-shaped.

*Margin*.—Repand.

*Venation*.—Pinnate.

*Surface texture*.—Glabrous, both upper and lower surfaces.

*Leaf blade* (*ratio of length to width*).—About 2:3.

*Angle at apex*.—Approximately 0-15 degrees.

*Angle at base*.—Approximately 1-5 degrees.

*Profile*.—Up folded.

*Leaf blade tip*.—In the plane of the leaf.

*Angle of tip*.—Mostly acute rarely obtuse.

*Undulation of margin*.—Medium.

Type 2 petiole:

*Average length*.—Approximately 1.4 cm.

*Average diameter*.—Approximately 1.2 mm.

*Color*.—About Medium Yellow-green 152D).

*Thickness*.—Medium, approximately 2.0 mm.

FLOWERS

General:

*Date of first bloom*.—About March 31.

*Location of first bloom*.—Apical flower bud of the cyme.

*Date of full bloom*.—About April 18.

*Date of end of bloom*.—About April 26.

*Time of bloom*.—Medium to late.

*Duration of bloom*.—Medium, approximately 25 days.

*Diameter of the fully open flower*.—Medium, approximately 4 mm.

*Flower aroma*.—Fragrant.

*Shape*.—Rosaceous regular flower actinomorphic.

*Number of flowers*.—Each cyme has 2 to 5 flowers. The flower inflorescence are compact and in clusters not born on elongated stems.

Peduncle:

*Length*.—Medium, approximately 10 mm.

*Color*.—About Medium Green-White 157B and Medium Green-White 157C.

*Pubescence*.—Absent, glabrous.

Petals:
*Number*.—Five.
*Arrangement*.—Free.
*Length*.—Medium, approximately 18 mm.
*Width*.—Medium, approximately 6 mm.
*Shape*.—Narrow acute.
*Apex shape*.—Pointed, tapers to tip "narrow acute'.
*Base shape*.—Rounded to flat at base, widest at middle of the petal.
*Color*.—Inner Surface: About White 155 B and White 155C. Inner Surface: About White 155 B and White 155C.
*Surface texture*.—Glabrous.
*Margins*.—Smooth.
*Frequency of flower with double petals*.—None.
*Pubescence of inner surface*.—Absent.
*Pubescence of outer surface*.—Absent.

Sepals (calyx consists of five sepals fused at the base and attached to the receptacle):
*Number*.—Five.
*Length*.—Approximately 3 mm.
*Diameter*.—Approximately 2 mm.
*Shape*.—Triangular and fused.
*Color*.—About Medium Green-White 157C.
*Surface texture*.—Glabrous.
*Margin*.—Smooth.
*Positioning*.—Touching receptacle.
*Pubescence of inner surface*.—Absent.
*Pubescence of outer surface*.—Absent.
*Frequency of flower with double sepals*.—None.

Stamens:
*Number*.—On average, range is 20 to 23.
*Length*.—Approximately 10-12 mm.
*Filament color*.—About White 155C.
*Anther color*.—About Medium Yellow-Orange 15B and Medium Yellow-Orange 15C.
*Pollen color*.—About Medium Yellow-Orange 15B and Medium Yellow-Orange 15C.
*Position*.—Tendency toward hypogynous.

Pistil:
*Number*.—One.
*Length*.—Approximately 15 mm.
*Ovary diameter*.—Approximately 3 mm.
*Pubescence*.—Glabrous.
*Stigma extension in comparison to anthers*.—Stigma exerted (protruding beyond) anthers.
*Frequency of supplementary pistils*.—Absent.

Flower-Buds:
*Hardiness*.—Tender.
*Size*.—Variable.
*Length*.—Variable, ranging from approximately 5 mm to approximately 12 mm.
*Shape*.—Plump.
*Positioning*.—Free.
*Pubescence*.—Glabrous.
*Color*.—About Medium Green-White 157C.

Receptacle:
*Depth*.—Shallow.
*Pubescence of inner surface*.—Glabrous.
*Pubescence of outer surface*.—Glabrous.

Stigma:
*Position* (*as compared with anthers*).—Above, exerted.

Anthers:
*Color* (*just before dehiscence*).—About Medium Yellow-Orange 15B and Medium Yellow-Orange 15C.

Pollen:
*Color*.—About Medium Yellow-Orange 15B and Medium Yellow-Orange 15C.

Ovary:
*Pubescence*.—Glabrous.

Style:
*Pubescence* (*of base*).—Glabrous.

FRUIT

General: (Description taken in central San Joaquin Valley, Calif. between June 1 and October 1).
*Date of last pick*.—Approximately end of September.
*Maturity when described*.—Firm, ripe condition.
*Season ripening*.—Early season ripening beginning in the middle of April. Late season ripening until the end of September. Optimal harvest window is May through August.
*Position of maximum diameter*.—Towards the middle.
*Shape*.—The diameter is consistently more than the length snaking the fruit shape slightly oblate ellipsoid.

Size:
*Length* (*stem end to apex*).—Approximately 6.5 cm to 7.7 cm with an average of 6.95 cm from fruit harvested in October. Overall length depends upon harvest date with fruit picked earlier in June at the smaller end of the range and fruit picked in October at the larger end of the range.
*Diameter in line with suture plane*.—Approximately 7.4 cm to 8.5 cm with an average of 7.75 cm from fruit harvested in October. Overall diameter depends upon harvest date with fruit picked earlier having a smaller diameter.
*Average weight*.—Approximately 182.6 gm to 294.6 gm with an average weight of 222.3 gm. Fruit picked later in the season has a greater weight compared to early season fruit.

Form:
*Viewed from apex*.—Rounded.
*Viewed from side, facing suture*.—The diameter is consistently greater than the length making the fruit shape slightly oblate ellipsoid.
*Viewed from side, perpendicular to suture*.—Rounded.

Apex shape: Rounded.

Fruit stem cavity:
*Shape*.—Circular.
*Depth*.—Shallow; Approximately 2 mm.
*Breadth*.—Approximately 1.5 cm.
*Width*.—Medium.

Fruit stem:
*Length*.—Medium; approximately 0.8 cm to 1.1 cm with average length of approximately 1.0 cm.
*Diameter*.—Approximately 0.3 cm.
*Apex cavity*.—Approximately 1 mm to 2 mm in depth and 15 mm in diameter. About Medium Yellow-Green 145B.
*Size of the columella in cross section*.—Medium to small, less than 5%.

Fruit skin:
*Thickness*.—Medium to thin.
*Adherence to flesh*.—Medium to strong.
*Surface texture*.—Medium and firm.
*Pubescence*.—None.
*Bloom*.—March.

*Rind color*.—The rind is very distinctly pigmented. There is a combination of colors constantly present on all of the fruits. The pattern and the percentage of the three most prevalent colors vary from fruit to fruit. Most noticeable is the reddish blush ranging from about Medium Greyed-Orange 168B to Medium Greyed-Orange 168C and Medium Greyed-Orange 170B. There is a green to yellow tinge to the exterior rind that is about Medium Greyed-Yellow 163B. There is also an orange tinge that is about Medium Yellow-Orange 21C. The reddish blush deepens in color as the fruit matures.

*Roughness*.—Absent.

*Tendency to crack*.—Slight to none. None in the wet season.

*Number of dents*.—None.

*Hardness to peeling*.—Moderate to difficult.

*Toughness of segment membrane*.—Medium.

Oil glands:

*Size*.—Small.

*Density*.—Medium, approximately 35 per cm2.

*Irregularity of oil glands*.—Regular.

Juice sac:

*Shape*.—Variable but mostly elongate.

*Size*.—Medium, approximately 8-10 mm in length by 2-4 mm in width.

*Color*.—Slightly colored.

*Amount*.—High to medium.

Number of segments per fruit: Approximately 11 segments.

Seeds: Lightly seeded 0-3 seeds.

Flesh:

*Ripens*.—Even.

*Texture*.—Firm and meaty.

*Flavor*.—Delicate.

*Brix*.—Fruits from the mutated Mother tree limb (five fruits in all) were harvested and tested for brix, acid, and sugar acid ratio (S/A) on July 1. The average results were Brix: 12.0, Acid: 0.51 and S/A ratio 23.9 Tests on the first harvest of 20 daughter and grand-daughter trees measured Brix 10.5, Acid: 0.53 and S/A ration: 20.0. The same trees were sampled on July 14 and tested Brix: 10.8, Acid: 0.49 and S/A ratio: 22.3.

*Juice*.—Abundant and about Dark Greyed-Orange 169A, Medium Greyed-Orange 169B, and Medium Greyed-Orange 169D.

*Aroma*.—Aromatic.

*Ground color*.—About Dark Greyed-Orange 169A, Medium Greyed-Orange 169B, and Medium Greyed-Orange 169D.

*Anthocyanin color of flesh*.—Absent. The coloration of the flesh is due to a combination of lycopenes and beta carotenes. This coloration is similar to the 'Cara Cara' navel orange.

*Acidity*.—Medium.

*Sugar content*.—Medium to high.

*Eating quality*.—Very good.

*Firmness*.—Firm.

Fruit use: Fresh market.

Fruit shipping and keeping quality: Good.

Resistance to insects and disease: There are no indications that there are any particular susceptibilities to insects or diseases noted.

What is claimed is:

1. A new and distinct *citrus* tree as herein described and illustrated.

* * * * *